United States Patent
Charles et al.

(10) Patent No.: US 11,577,079 B2
(45) Date of Patent: Feb. 14, 2023

(54) DEEP BRAIN STIMULATION IN EARLY STAGE PARKINSON'S

(71) Applicant: VANDERBILT UNIVERSITY, Nashville, TN (US)

(72) Inventors: David Charles, Nashville, TN (US); Mallory Hacker, Nashville, TN (US); Peter Konrad, Franklin, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 267 days.

(21) Appl. No.: 16/500,986

(22) PCT Filed: Mar. 27, 2018

(86) PCT No.: PCT/US2018/024469
§ 371 (c)(1),
(2) Date: Oct. 4, 2019

(87) PCT Pub. No.: WO2018/187080
PCT Pub. Date: Oct. 11, 2018

(65) Prior Publication Data
US 2020/0188672 A1    Jun. 18, 2020

Related U.S. Application Data (60) Provisional application No. 62/482,879, filed on Apr. 7, 2017.

(51) Int. Cl.
*A61N 1/36* (2006.01)
*A61N 1/05* (2006.01)
*C12Q 1/68* (2018.01)
*C12Q 1/6883* (2018.01)
*A61P 25/16* (2006.01)
*A61K 45/06* (2006.01)

(52) U.S. Cl.
CPC ....... *A61N 1/36067* (2013.01); *A61N 1/0534* (2013.01); *A61K 45/06* (2013.01); *A61P 25/16* (2018.01)

(58) Field of Classification Search
CPC .... A61N 1/0534; A61N 1/36067; A61N 1/36; A61P 25/16
See application file for complete search history.

(56) References Cited

U.S. PATENT DOCUMENTS

| | | |
|---|---|---|
| 5,716,377 A | 2/1998 | Rise et al. |
| 9,295,838 B2 | 3/2016 | Starr et al. |
| 9,498,628 B2 | 11/2016 | Kaemmerer et al. |

(Continued)

OTHER PUBLICATIONS

Caire et al., "Subthalamic nucleus location: relationships between stereotactic AC-PC-based diagrams and MRI anatomy-based contours", *Stereotact. Funct. Neurosurg.*, 87:337-347, 2009.

(Continued)

*Primary Examiner* — Jon Eric C Morales
(74) *Attorney, Agent, or Firm* — Parker Highlander PLLC (57) ABSTRACT

The present disclosure relates to the treatment of patients with Parkinson's Disease using subthalmic nucleus deep brain stimulation to a specific region of the brain. By positioning the electrode in the margin of the dorsal-lateral and anterior region of the subthalamic nucleus, improved benefits are obtained.

18 Claims, 2 Drawing Sheets

(56) References Cited

U.S. PATENT DOCUMENTS

| | | | |
|---|---|---|---|
| 2005/0065427 A1* | 3/2005 | Magill | A61N 1/3605 600/407 |
| 2006/0017749 A1 | 1/2006 | McIntyre et al. | |
| 2006/0173509 A1 | 8/2006 | Lee et al. | |
| 2006/0184209 A1 | 8/2006 | John et al. | |
| 2014/0163627 A1 | 6/2014 | Starr et al. | |
| 2015/0352363 A1 | 12/2015 | McIntyre et al. | |
| 2016/0319355 A1* | 11/2016 | Charles | G01N 33/6896 |

OTHER PUBLICATIONS

Charles et al., "Subthalamic nucleus deep brain stimulation in early stage Parkinson's disease", *Parkinsonism & Related Disorders*, 20(7):731, 2014.

Extended Search Report and Opinion issued in corresponding European Application No. 18780849, dated Dec. 16, 2020.

Gross et al., "Electrophysiological Mapping for the Implantation of Deep Brain Stimulators for Parkinson's Disease and Tremor", *Movement Dis.*, 21(Suppl. 14):S259-S283, 2006.

Herzog et al., "Most effective stimulation site in subthalamic deep brain stimulation for Parkinson's disease", *Mov. Disord.*, 19(9):1050-1054, 2004.

Hutchinson et al., "Neurophysiological Identification of the Subthalamic Nucleus in Surgery for Parkinson's Disease", *Ann. Neurol.*, 44(4):622-628, 1998.

International Preliminary Report on Patentability issued in corresponding PCT Application No. PCT/US2018/024469, dated Oct. 17, 2019.

International Search Report and Written Opinion issued in corresponding PCT Application No. PCT/US2018/024469, dated Jun. 14, 2018.

McClelland et al., "Typical variations of subthalamic electrode location do not predict limb motor function improvement in Parkinson's disease", *J. Clin. Neurosci.*, 16:771-778, 2009.

Plaha et al., "Stimulation of the caudal zona incerta is superior to stimulation of the subthalamic nucleus in improving contralateral parkinsonism", *Brain*, 129(7):1732-1747, 2006.

Schlaier et al., "Deep brain stimulation in Parkinson's disease: motor effects relative to the MRI-defined STN", *Neurosurg. Rev.*, 37:461-470, 2014.

Schuepbach et al., "Neurostimulation for Parkinson's disease with early motor complications", *N. Engl. J. Med.*, 368(7):610-622, 2013.

Starr, "Placement of Deep Brain Stimulators into the Subthalamic Nucleus or Globus pallidus internus: Technical Approach", *Stereotact. Funct. Neurosurg.*, 79:118-145, 2002.

U.S. Appl. No. 15/642,440, entitled "Therapeutic Response in Parkinson's Disease," by Mallory L. Hacker and David Charles, filed Jul. 6, 2017.

Voges et al., "Bilateral high-frequency stimulation in the subthalamic nucleus for the treatment of Parkinson disease: correlation of therapeutic effect with anatomical electrode position", *J. Neurosurg.*, 96(2):269-279, 2002.

Wodarg et al., "Stimulation site within the MRI-defined STN predicts postoperative motor outcome", *Mov. Disord.*, 27(7):874-9, 2012.

Yelnik et al., "Localization of stimulating electrodes in patients with Parkinson disease by using a three-dimensional atlas—magnetic resonance imaging coregistration method", *J. Neurosurg.*, 99(1):89-99, 2003.

* cited by examiner

DEEP BRAIN STIMULATION IN EARLY STAGE PARKINSON'S

PRIORITY CLAIM

This application is a national phase application under 35 U.S.C. § 371 of International Application No. PCT/US2018/024469, filed Mar. 27, 2018, which claims benefit of priority to U.S. Provisional Application Ser. No. 62/482,879, filed Apr. 7, 2017, the entire contents of each of which are hereby incorporated by reference.

This invention was made with government support under grant no. R01-EB006136 awarded by the National Institutes of Health and grant no. UL1TR00001 awarded by the National Institutes of Health/National Center for Advancing Translational Sciences. The government has certain rights in the invention.

BACKGROUND

I. Field

The present disclosure relates to the fields medicine, central nervous system disorders and neurobiology. More particularly, the disclosure relates to an improved method of performing subthalmic nucleus deep brain stimulation on a subject afflicted with Parkinson's Disease.

II. Related Art

Parkinson's disease (PD) is a long-term degenerative disorder of the central nervous system that mainly affects the motor system. The symptoms generally come on slowly over time. Early in the disease, the most obvious are shaking, rigidity, slowness of movement, and difficulty with walking. Thinking and behavioral problems may also occur, and dementia becomes common in the advanced stages of the disease, as well as depression and anxiety (see in more than a third of PD patients). Other symptoms include sensory, sleep, and emotional problems. Thus, PD, is a devastating disease with very limited treatment options; no cure is known.

Preclinical models of early stage PD demonstrate the potential for subthalmic nucleus deep brain stimulation (STN-DBS) to slow disease progression (Wallace et al., 2007; Spieles-Engemann et al., 2010)). However, there is no clinical evidence to support the hypothesis that STN-DBS can in fact slow the progression of Parkinson's disease motor symptoms. The following is a survey of some of these studies.

Plaha et al. (2006), in an observational study on 35 subjects, showed that the zona incerta nucleus (cZI) is superior to the STN in improving contralateral motor scores for the treatment of medically refractory Parkinson's disease while bilateral stimulation medial/dorsomedial to the STN is associated with speech and balance problems.

McClelland et al. (2009) examined 42 electrode tip locations. The coordinates of the intended targets were not different between groups, indicating that differences between the groups could not be explained by differences in STN targeting. The two groups were similar in electrode tip location ($p>0.05$) with regard to 3D distance ($p=0.759$), lateral-medial (x) axis distance ($p=0.983$), anterior-posterior (y) axis distance ($p=0.949$) or superior-inferior (z) axis distance ($p=0.894$) from the intended anatomical target at 80% power, a sample size of 1355 electrodes in each group would be needed to detect a significant difference with regard to 3D distance.

Caire et al. (2009) examined 22 subjects and showed that STN stereotactic AC-PC-based diagrams are not perfectly representative of the STN, at least as determined on MRI. The MRI-localized STN tends to be located more posteriorly and medially than the probabilistic location proposed by stereotactic AC-PC-based diagrams.

Schlaier et al. (2014) examined 22 subjects and found a statistically significant correlation between location and improvement of bradykinesia. The more lateral the stimulation site was located in the MRI-STN, the more pronounced the improvement of the contralateral akinesia.

Herzog et al, (2004) looked at 14 subjects using 25 electrode locations. Their results demonstrate that DBS either at the dorsolateral border of the STN or within STN is most effective in terms of motor improvement and energy consumption.

Voges et al, (2002) examined 15 subjects and found that the degree of clinical improvement differed little, on average, for active contacts lying within the STN, within the border zone of the STN and subthalamic white matter, or within subthalamic fibers, as defined by MR reconstruction. If the ratio of clinical improvement and necessary stimulation energy was taken as a measure for clinical efficacy, a trend for better results became evident for active poles projecting onto subthalamic fiber tracts compared with those placed either inside the STN or at the STN-fiber interfaces.

Yelnik et al. (2003) examined 10 subjects and found that stimulation applied through distant contacts improved parkinsonian symptoms when the contacts were located in the STN. Contacts located in other structures were associated with variable effects ranging from worsening to improvement of symptoms, but the use of some had a positive effect on all four symptoms.

Wodarg et al. (2012) examined 35 subjects. ANCOVA revealed that only the position of the active stimulation contact relative to the diagonal STN axis significantly influenced improvement of the lateralized UPDRS-III at 6 ($F(1, 8)=14.012$; $P<0.0001$) and 36 months follow-up ($F(1,8)=7.484$; $P<0.013$). Other variables had no bearing. ANCOVA revealed that only the contact position within STN quadrants significantly influenced the improvement of the total UPDRS-III after 6 ($F(1,8)=14.079$; $P<0.0001$) and 36 months ($F(1,8)=12.495$; $P<0.001$). Patients with both active contacts in lateral quadrants had a significantly better postoperative motor outcome compared to patients with two medial contacts or one medial and one lateral contact. In lateral quadrants, the voltage threshold for contractions (3.9 V; SD, 0.5) and dysarthria (3.8 V; SD, 0.6) was significantly lower than in medial quadrants (4.9 [SD, 0.4] and 4.7 [SD, 0.3] V) ($P<0.001$). On the other hand, chronic stimulation amplitudes after 36 months were also significantly lower for lateral (3.0 V; SD, 0.7) than for medial contacts (3.6 V SD, 0.6) ($P<0.001$), allowing a comparable therapeutic window.

In some, while many publications report efficacy using STN-DBS to treat motor symptoms, there is not a clear indication that a particular region of the brain is most efficacious for outcome. Nonetheless, STN-DBS is the current standard of care and helps address symptoms. However, the underlying disease continues to progress relentlessly. No study to date has shown an effect from STN-DBS on the progression of PD motor symptoms.

SUMMARY

In accordance with the present disclosure, there is provided a method of treating Parkinson's Disease (PD) in a subject comprising administering to said subject subthalmic nucleus (STN) deep brain stimulation (DBS) by positioning a DBS electrode in the margin of the dorsal-lateral and anterior region of the subthalamic nucleus and applying electrical current to said subject through said electrode. The subject may be a human subject, such as a male or female human subject. The subject may be anon-human mammalian subject. The subject may be an early stage PD subject. The DBS may be performed more than once, such as on a chronic basis.

The method may further comprise treating said subject with a second PD therapy, for example, where the second PD therapy is administered prior to STN-DBS, or is administered at the same time as STN-DBS, or is administered after STN-DBS. The second PD therapy may be selected from levodopa, optionally in combination with a DOPA decarboxylase inhibitor (carbidopa, benserazide) or a COMT inhibitor (tolcapone, entacapone), a dopamine agonist (e.g., apomorphine, bromocriptine, pergolide, pramipexole, ropinirole, piribedil, cabergoline, apomorphine, lisuride), an MAO-B inhibitor (e.g., safinamide, selegiline, rasagiline), amantadine, an anticholinergics cholinesterase inhibitor, and lesional surgery, or combinations thereof.

The STN-DBS may result in one or more of slowing of motor symptom progression, stopping motor symptom progression, and/or reversing motor symptom progression, or may result in one or more of lower stimulation parameters, less need for post-operative dopaminergic medication, and/or less development of levodopa associated dyskinesia or other motor fluctuations.

The margin of the dorsal-lateral and anterior region of the subthalamic nucleus may be defined by imaging and/or micro-electrode recording that defines the subthalamic nucleus. Imaging may comprise (a) preoperative imaging and preoperative stereotactic target planning and trajectory assignment; and (b) stereotactic mapping of the STN nucleus bilaterally. The margin of the dorsal-lateral and anterior region of the subthalamic nucleus may be defined electrophysiologically by the anterior border of STN through its relationship with the internal capsule (having its characteristic findings—stimulation causes contraction or motor effects, and recordings are relatively silent) and the dorsal margin of STN (defined by increased neuronal firing upon transition from white matter tracts—relatively silent—to STN nucleus—relatively high firing frequency and low-amplitude, high frequency neuronal cell firing). Electrophysiologic identification may comprise the insertion of microelectrodes into the region of STN, having an exposed recording surface small enough to detect unit firing activity as measured by impedance greater than 150K ohms, and continuous measurement of spontaneous neural firing activity while passing the microelectrodes through the region dorsal to STN and into the STN. The firing rate shall change significantly upon transitioning from white matter tracts just above or anterior to the STN to the neuronal activity seen within the STN by a factor of 5 or more.

In yet another embodiment, there is provided an agent effective to treat Parkinson's Disease (PD) for use in treating PD in a subject, wherein the subject is administered subject subthalmic nucleus (STN) deep brain stimulation (DBS) by positioning a DBS electrode in the margin of the dorsal-lateral and anterior region of the subthalamic nucleus and applying electrical current to said subject through said electrode. The agent effective to treat PD may be selected from levodopa, optionally in combination with a DOPA decarboxylase inhibitor (carbidopa, benserazide) or a COMT inhibitor (tolcapone, entacapone), a dopamine agonist (e.g., apomorphine, bromocriptine, pergolide, pramipexole, ropinirole, piribedil, cabergoline, apomorphine, lisuride), an MAO-B inhibitor (e.g., safinamide, selegiline, rasagiline), amantadine, an anticholinergics cholinesterase inhibitor, and lesional surgery, or combinations thereof. The agent effect to treat PD may be administered prior to STN-DBS, at the same time as STN-DBS, and/or after STN-DBS.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, for the method being employed to determine the value, or that exists among the study subjects. Such an inherent variation may be a variation of ±10% of the stated value.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIGS. 1A-D: STN Maps. Maps of volumes of activation in left (FIGS. 1A-B) and right (FIGS. 1C-D) STN DBS based on programming of Medtronic 3389 implants at 24 months shown overlaide on the 7T MRI in the CranialVault atlas; (FIG. 1A, FIG. 1C) for 9 cases where UPDRS-III OFF motor symptoms worsened from baseline to 24 months and (FIG. 1B, FIG. 1D) for 5 cases for UPDRS-III OFF motor symptoms did not worsen from baseline to 24 months.

DETAILED DESCRIPTION

The inventors completed the only prospective, randomized, controlled, single-blind clinical trial investigating bilateral subthalamic nucleus deep brain stimulation (STN-DBS) in very early stage Parkinson's disease (PD). This safety and tolerability trial met its primary outcome (1), and the FDA approved the conduct of a multicenter, pivotal trial of DBS in early stage PD (IDE # G050016). The pilot trial included multiple, seven-day washouts of all PD therapeutics (medication and stimulation, if applicable) to make the best attempt to capture the underlying state of early PD motor symptoms (Charles et al., 2014).

Given the clinical heterogeneity among Parkinson's disease patients, the inventors conducted a post hoc analysis of individual subjects' motor symptom worsening after two years of treatment with optimal drug therapy (ODT) alone or DBS+ODT. They found that the lateral-inferior position of the stimulating contact within the STN led to slowing motor symptom progression, lower stimulation parameters, and less need for post-operative dopaminergic medication. These and other aspects of the disclosure are set forth below.

I. Parkinson's Disease

Parkinson's disease (PD) is a long-term degenerative disorder of the central nervous system that mainly affects the motor system. The symptoms generally come on slowly over time. Early in the disease, the most obvious are shaking, rigidity, slowness of movement, and difficulty with walking. Thinking and behavioral problems may also occur. Dementia becomes common in the advanced stages of the disease. Depression and anxiety are also common occurring in more than a third of people with PD. Other symptoms include sensory, sleep, and emotional problems. The main motor symptoms are collectively called "parkinsonism", or a "parkinsonian syndrome."

The cause of Parkinson's disease is generally unknown, but believed to involve both genetic and environmental factors. Those with a family member affected are more likely to get the disease themselves. There is also an increased risk in people exposed to certain pesticides and among those who have had prior head injuries while there is a reduced risk in tobacco smokers and those who drink coffee or tea. The motor symptoms of the disease result from the death of cells in the substantia nigra, a region of the midbrain. This results in not enough dopamine in these areas. The reason for this cell death is poorly understood, but involves the build-up of proteins into Lewy bodies in the neurons. Diagnosis of typical cases is mainly based on symptoms, with tests such as neuroimaging being used to rule out other diseases.

There is no cure for Parkinson's disease. Initial treatment is typically with the anti-parkinson medication L-DOPA (levodopa), with dopamine agonists being used once levodopa becomes less effective. As the disease progresses and neurons continue to be lost, these medications become less effective while at the same time they produce a complication marked by involuntary writhing movements. Diet and some forms of rehabilitation have shown some effectiveness at improving symptoms. Surgery to place microelectrodes for deep brain stimulation has been used to reduce motor symptoms in severe cases where drugs are ineffective. Evidence for treatments for the non-movement-related symptoms of PD, such as sleep disturbances and emotional problems, is less strong.

In 2013, PD was present in 53 million people and resulted in about 103,000 deaths globally. Parkinson's disease typically occurs in people over the age of 60, of which about one percent are affected. Males are more often affected than females. When it is seen in people before the age of 40 or 50, it is called young onset PD. The average life expectancy following diagnosis is between 7 and 14 years.

The term parkinsonism is used for a motor syndrome whose main symptoms are tremor at rest, stiffness, slowing of movement and postural instability. Parkinsonian syndromes can be divided into four subtypes, according to their origin (1) primary or idiopathic, (2) secondary or acquired, (3) hereditary parkinsonism, and (4) Parkinson plus syndromes or multiple system degeneration.

Parkinson's disease is the most common form of parkinsonism and is usually defined as "primary" parkinsonism, meaning parkinsonism with no external identifiable cause. In recent years several genes that are directly related to some cases of Parkinson's disease have been discovered. As much as this conflicts with the definition of Parkinson's disease as an idiopathic illness, genetic parkinsonism disorders with a similar clinical course to PD are generally included under the Parkinson's disease label. The terms "familial Parkinson's disease" and "sporadic Parkinson's disease" can be used to differentiate genetic from truly idiopathic forms of the disease.

Usually classified as a movement disorder, PD also gives rise to several non-motor types of symptoms such as sensory deficits, cognitive difficulties, and sleep problems. Parkinson plus diseases are primary parkinsonisms which present additional features. They include multiple system atrophy, progressive supranuclear palsy, corticobasal degeneration, and dementia with Lewy bodies.

In terms of pathophysiology, PD is considered a synucleiopathy due to an abnormal accumulation of alpha-synuclein protein in the brain in the form of Lewy bodies, as opposed to other diseases such as Alzheimer's disease where the brain accumulates tau protein in the form of neurofibrillary tangles. Nevertheless, there is clinical and pathological overlap between tauopathies and synucleinopathies. The most typical symptom of Alzheimer's disease, dementia, occurs in advanced stages of PD, while it is common to find neurofibrillary tangles in brains affected by PD. Dementia with Lewy bodies (DLB) is another synucleinopathy that has similarities with PD, and especially with the subset of PD cases with dementia. However, the relationship between PD and DLB is complex and still has to be clarified. They may represent parts of a continuum or they may be separate diseases.

A. Signs and Symptoms

Parkinson's disease affects movement, producing motor symptoms. Non-motor symptoms, which include autonomic dysfunction, neuropsychiatric problems (mood, cognition, behavior or thought alterations), and sensory and sleep difficulties, are also common. Some of these non-motor symptoms are often present at the time of diagnosis and can precede motor symptoms.

Four motor symptoms are considered cardinal in PD: tremor, rigidity, slowness of movement, and postural instability. Tremor is the most apparent and well-known symptom. It is the most common; though around 30% of individuals with PD do not have tremor at disease onset, most develop it as the disease progresses. It is usually a rest tremor—maximal when the limb is at rest and disappearing with voluntary movement and sleep. It affects to a greater extent the most distal part of the limb and at onset typically appears in only a single arm or leg, becoming bilateral later. Frequency of PD tremor is between 4 and 6 hertz (cycles per second). A feature of tremor is pill-rolling, the tendency of the index finger of the hand to get into contact with the thumb and perform together a circular movement. The term derives from the similarity between the movement of people with PD and the earlier pharmaceutical technique of manually making pills.

Bradykinesia is another characteristic feature of PD, and is a slowness in the execution of movement. Performance of sequential and simultaneous movement is hindered. Initial manifestations are problems when performing daily tasks which require fine motor control such as writing, sewing or getting dressed. Clinical evaluation is based on similar tasks such as alternating movements between both hands or between both feet. Bradykinesia is not equal for all movements or times. It is modified by the activity or emotional state of the subject, to the point that some people are barely able to walk yet can still ride a bicycle. Generally people with PD have less difficulty when some sort of external cue is provided.

Rigidity is stiffness and resistance to limb movement caused by increased muscle tone, an excessive and continuous contraction of muscles. In parkinsonism the rigidity can be uniform (lead-pipe rigidity) or ratchety (cogwheel rigidity). The combination of tremor and increased tone is considered to be at the origin of cogwheel rigidity. Rigidity may be associated with joint pain; such pain being a frequent initial manifestation of the disease. In early stages of Parkinson's disease, rigidity is often asymmetrical and it tends to affect the neck and shoulder muscles prior to the muscles of the face and extremities. With the progression of the disease, rigidity typically affects the whole body and reduces the ability to move.

Postural instability is typical in the late stages of the disease, leading to impaired balance and frequent falls, and secondarily to bone fractures. Instability is often absent in the initial stages, especially in younger people. Up to 40% may experience falls and around 10% may have falls weekly, with the number of falls being related to the severity of PD.

Other recognized motor signs and symptoms include gait and posture disturbances such as festination (rapid shuffling steps and a forward-flexed posture when walking), speech and swallowing disturbances including voice disorders, mask-like face expression or small handwriting, although the range of possible motor problems that can appear is large.

Parkinson's disease can cause neuropsychiatric disturbances, which can range from mild to severe. This includes disorders of speech, cognition, mood, behavior, and thought. Cognitive disturbances can occur in the early stages of the disease and sometimes prior to diagnosis, and increase in prevalence with duration of the disease. The most common cognitive deficit in affected individuals is executive dysfunction, which can include problems with planning, cognitive flexibility, abstract thinking, rule acquisition, initiating appropriate actions and inhibiting inappropriate actions, working memory, and selecting relevant sensory information. Fluctuations in attention, impaired perception and estimation of time, slowed cognitive processing speed are among other cognitive difficulties. Memory is affected, specifically in recalling learned information. Nevertheless, improvement appears when recall is aided by cues. Visuospatial difficulties are also part of the disease, seen for example when the individual is asked to perform tests of facial recognition and perception of the orientation of drawn lines.

A person with PD has an increased risk of dementia compared to the general population. The prevalence of dementia increases with duration of the disease. Dementia is associated with a reduced quality of life in people with PD and their caregivers, increased mortality, and a higher probability of needing nursing home care.

Behavior and mood alterations are more common in PD without cognitive impairment than in the general population and are usually present in PD with dementia. The most frequent mood difficulties are depression, apathy and anxiety. Establishing the diagnosis of depression is complicated by symptoms that often occur in Parkinson's including dementia, decreased facial expression, decreased movement, a state of indifference, and quiet speech. Impulse control behaviors such as medication overuse and craving, binge eating, hypersexuality, or problem gambling can appear in PD and have been related to the medications used to manage the disease. Psychotic symptoms—hallucinations or delusions—occur in 4% of people with PD, and it is assumed that the main precipitant of psychotic phenomena in Parkinson's disease is dopaminergic excess secondary to treatment; it therefore becomes more common with increasing age and levodopa intake.

In addition to cognitive and motor symptoms, PD can impair other body functions. Sleep problems are a feature of the disease and can be worsened by medications. Symptoms can manifest as daytime drowsiness, disturbances in REM sleep, or insomnia. A systematic review shows that sleep attacks occur in 13.0% of patients with Parkinson's disease on dopaminergic medications.

Alterations in the autonomic nervous system can lead to orthostatic hypotension (low blood pressure upon standing), oily skin and excessive sweating, urinary incontinence and altered sexual function. Constipation and gastric dysmotility can be severe enough to cause discomfort and even endanger health. PD is related to several eye and vision abnormalities such as decreased blink rate, dry eyes, deficient ocular pursuit (eye tracking) and saccadic movements (fast automatic movements of both eyes in the same direction), difficulties in directing gaze upward, and blurred or double vision. Changes in perception may include an impaired sense of smell, sensation of pain and paresthesia (skin tingling and numbness). All of these symptoms can occur years before diagnosis of the disease.

B. Causes

Parkinson's disease in most people is idiopathic (having no specific known cause). However, a small proportion of cases can be attributed to known genetic factors. Other factors have been associated with the risk of developing PD, but no causal relationships have been proven.

A number of environmental factors have been associated with an increased risk of Parkinson's, including pesticide exposure, head injuries, and living in the country or farming. Rural environments and the drinking of well water may be risks, as they are indirect measures of exposure to pesticides. Implicated agents include insecticides, primarily chlorpyrifos and organochlorines and pesticides, such as rotenone or paraquat, and herbicides, such as Agent Orange and ziram. Exposure to heavy metals has been proposed to be a risk factor, through possible accumulation in the substantia nigra, but studies on the issue have been inconclusive.

PD traditionally has been considered a non-genetic disorder; however, around 15% of individuals with PD have a first-degree relative who has the disease. At least 5% of people are now known to have forms of the disease that occur because of a mutation of one of several specific genes.

Mutations in specific genes have been conclusively shown to cause PD. These genes code for alpha-synuclein (SNCA), parkin (PRKN), leucine-rich repeat kinase 2 (LRRK2 or dardarin), PTEN-induced putative kinase 1 (PINK1), DJ-1 and ATP13A2. In most cases, people with these mutations will develop PD. With the exception of LRRK2, however, they account for only a small minority of cases of PD. The most extensively studied PD-related genes are SNCA and LRRK2. Mutations in genes including SNCA, LRRK2 and glucocerebrosidase (GBA) have been found to be risk factors for sporadic PD. Mutations in GBA are known to cause Gaucher's disease. Genome-wide association studies, which search for mutated alleles with low penetrance in sporadic cases, have now yielded many positive results.

The role of the SNCA gene is important in PD, because the alpha-synuclein protein is the main component of Lewy bodies. Missense mutations of the gene (in which a single nucleotide is changed), and duplications and triplications of the locus containing it have been found in different groups with familial PD. Missense mutations are rare. On the other hand, multiplications of the SNCA locus account for around 2% of familial cases. Multiplications have been found in asymptomatic carriers, which indicate that penetrance is incomplete or age-dependent.

The LRRK2 gene (PARK8) encodes a protein called dardarin. The name dardarin was taken from a Basque word for tremor, because this gene was first identified in families from England and the north of Spain. Mutations in LRRK2 are the most common known cause of familial and sporadic PD, accounting for approximately 5% of individuals with a family history of the disease and 3% of sporadic cases. There are many mutations described in LRRK2, however unequivocal proof of causation only exists for a few.

Several Parkinson-related genes are involved in the function of lysosomes, organelles that digest cellular waste products. It has been suggested that some forms of Parkinson may be caused by lysosome dysfunctions that reduce the ability of cells to break down alpha-synuclein.

C. Diagnosis

A physician will diagnose Parkinson's disease from the medical history and a neurological examination. There is no medical test that will clearly identify the disease, but brain scans are sometimes used to rule out disorders that could give rise to similar symptoms. People may be given levodopa and resulting relief of motor impairment tends to confirm the diagnosis. The finding of Lewy bodies in the midbrain on autopsy is usually considered proof that the person had Parkinson's disease. The progress of the illness over time may reveal it is not Parkinson's disease, and some authorities recommend that the diagnosis should be periodically reviewed.

Other causes that can secondarily produce a parkinsonian syndrome are Alzheimer's disease, multiple cerebral infarction and drug-induced parkinsonism. Parkinson-plus syndromes such as progressive supranuclear palsy and multiple system atrophy must be ruled out. Anti-Parkinson's medications are typically less effective at controlling symptoms in Parkinson-plus syndromes. Faster progression rates, early cognitive dysfunction or postural instability, minimal tremor or symmetry at onset may indicate a Parkinson-plus disease rather than PD itself. Genetic forms are usually classified as PD, although the terms "familial Parkinson's disease" and "familial parkinsonism" are used for disease entities with an autosomal dominant or recessive pattern of inheritance.

Medical organizations have created diagnostic criteria to ease and standardize the diagnostic process, especially in the early stages of the disease. The most widely known criteria come from the UK Parkinson's Disease Society Brain Bank and the U.S. National Institute of Neurological Disorders and Stroke. The PD Society Brain Bank criteria require slowness of movement (bradykinesia) plus either rigidity, resting tremor, or postural instability. Other possible causes of these symptoms need to be ruled out. Finally, three or more of the following features are required during onset or evolution: unilateral onset, tremor at rest, progression in time, asymmetry of motor symptoms, response to levodopa for at least five years, clinical course of at least ten years and appearance of dyskinesias induced by the intake of excessive levodopa. Accuracy of diagnostic criteria evaluated at autopsy is 75-90%, with specialists such as neurologists having the highest rates.

Computed tomography (CT) and conventional magnetic resonance imaging (MRI) brain scans of people with PD usually appear normal. These techniques are nevertheless useful to rule out other diseases that can be secondary causes of parkinsonism, such as basal ganglia tumors, vascular pathology and hydrocephalus. A specific technique of MRI, susceptibility weighted imaging has been found to differentiate between patients and subjects without the disease and another technique, diffusion MRI, has been reported to be useful at discriminating between typical and atypical parkinsonism, although its exact diagnostic value is still under investigation. Dopaminergic function in the basal ganglia can be measured with different PET and SPECT radioactive tracers. Examples are ioflupane ($^{123}$I) (trade name DaTSCAN) and iometopane (Dopascan) for SPECT or fluorodeoxyglucose ($^{18}$F) and DTBZ for PET. A pattern of reduced dopaminergic activity in the basal ganglia can aid in diagnosing PD.

D. Prevention, Management, Rehabilitation and Palliative Care

Exercise in middle age reduces the risk of Parkinson's disease later in life. Caffeine also appears protective with a greater decrease in risk occurring with a larger intake of caffeinated beverages such as coffee. Although tobacco smoke causes adverse health effects, decreases life expectancy and quality of life, it may reduce the risk of PD by a third when compared to non-smokers. The basis for this effect is not known, but possibilities include an effect of nicotine as a dopamine stimulant. Tobacco smoke contains compounds that act as MAO inhibitors that also might contribute to this effect.

Antioxidants, such as vitamins C and D, have been proposed to protect against the disease, but results of studies have been contradictory and no positive effect has been proven. The results regarding fat and fatty acids have been contradictory, with various studies reporting protective effects, risk-increasing effects or no effects. Also, there have been preliminary indications of a possible protective role of estrogens and anti-inflammatory drugs.

There is no cure for Parkinson's disease, but medications, surgery, and multidisciplinary management can provide relief from the symptoms. The main families of drugs useful for treating motor symptoms are levodopa (usually combined with a dopa decarboxylase inhibitor or COMT inhibitor that does not cross the blood-brain barrier), dopamine agonists and MAO-B inhibitors. The stage of the disease determines which group is most useful. Two stages are usually distinguished: an initial stage in which the individual with PD has already developed some disability for which he needs pharmacological treatment, then a second stage in which an individual develops motor complications related to levodopa usage. Treatment in the initial stage aims for an optimal tradeoff between good symptom control and side-effects resulting from improvement of dopaminergic function. The start of levodopa treatment may be delayed by using other medications such as MAO-B inhibitors and dopamine agonists, in the hope of delaying the onset of dyskinesias. In the second stage the aim is to reduce symptoms while controlling fluctuations of the response to medication. Sudden withdrawals from medication or overuse have to be managed. When medications are not enough to control symptoms, surgery and deep brain stimulation can be of use. In the final stages of the disease, palliative care is provided to improve quality of life.

Levodopa has been the most widely used treatment for over 30 years. L-DOPA is converted into dopamine in the dopaminergic neurons by dopa decarboxylase. Since motor symptoms are produced by a lack of dopamine in the substantia nigra, the administration of L-DOPA temporarily diminishes the motor symptoms.

Only 5-10% of L-DOPA crosses the blood-brain barrier. The remainder is often metabolized to dopamine elsewhere, causing a variety of side effects including nausea, dyskinesias and joint stiffness. Carbidopa and benserazide are peripheral dopa decarboxylase inhibitors, which help to prevent the metabolism of L-DOPA before it reaches the dopaminergic neurons, therefore reducing side effects and increasing bioavailability. They are generally given as combination preparations with levodopa. Existing preparations are carbidopa/levodopa (co-careldopa) and benserazide/levodopa (co-beneldopa). Levodopa has been related to dopamine dysregulation syndrome, which is a compulsive overuse of the medication, and punding. There are slow release versions of levodopa in the form intravenous and intestinal infusions that spread out the effect of the medication. These slow-release levodopa preparations have not shown an increased control of motor symptoms or motor complications when compared to immediate release preparations.

Tolcapone inhibits the COMT enzyme, which degrades dopamine, thereby prolonging the effects of levodopa. It has been used to complement levodopa; however, its usefulness is limited by possible side effects such as liver damage. A similarly effective drug, entacapone, has not been shown to cause significant alterations of liver function. Licensed preparations of entacapone contain entacapone alone or in combination with carbidopa and levodopa.

Levodopa preparations lead in the long term to the development of motor complications characterized by involuntary movements called dyskinesias and fluctuations in the response to medication. When this occurs a person with PD can change from phases with good response to medication and few symptoms ("on" state), to phases with no response to medication and significant motor symptoms ("off" state). For this reason, levodopa doses are kept as low as possible while maintaining functionality. Delaying the initiation of therapy with levodopa by using alternatives (dopamine agonists and MAO-B inhibitors) is common practice. A former strategy to reduce motor complications was to withdraw L-DOPA medication for some time. This is discouraged now since it can bring dangerous side effects such as neuroleptic malignant syndrome. Most people with PD will eventually need levodopa and later develop motor side effects.

Several dopamine agonists that bind to dopaminergic post-synaptic receptors in the brain have similar effects to levodopa. These were initially used for individuals experiencing on-off fluctuations and dyskinesias as a complementary therapy to levodopa; they are now mainly used on their own as an initial therapy for motor symptoms with the aim of delaying motor complications. When used in late PD they are useful at reducing the off periods. Dopamine agonists include bromocriptine, pergolide, pramipexole, ropinirole, piribedil, cabergoline, apomorphine and lisuride.

Dopamine agonists produce significant, although usually mild, side effects including drowsiness, hallucinations, insomnia, nausea, and constipation. Sometimes side effects appear even at a minimal clinically effective dose, leading the physician to search for a different drug. Compared with levodopa, dopamine agonists may delay motor complications of medication use, but are less effective at controlling symptoms. Nevertheless, they are usually effective enough to manage symptoms in the initial years. They tend to be more expensive than levodopa. Dyskinesias due to dopamine agonists are rare in younger people who have PD, but along with other side effects, become more common with age at onset. Thus dopamine agonists are the preferred initial treatment for earlier onset, as opposed to levodopa in later onset. Agonists have been related to impulse control disorders (such as compulsive sexual activity and eating, and pathological gambling and shopping) even more strongly than levodopa.

Apomorphine, a non-orally administered dopamine agonist, may be used to reduce off periods and dyskinesia in late PD. It is administered by intermittent injections or continuous subcutaneous infusions. Since secondary effects such as confusion and hallucinations are common, individuals receiving apomorphine treatment should be closely monitored. Two dopamine agonists that are administered through skin patches (lisuride and rotigotine) and are useful for people in the initial stages and possibly to control off states in those in the advanced state.

MAO-B inhibitors (safinamide, selegiline and rasagiline) increase the level of dopamine in the basal ganglia by blocking its metabolism. They inhibit monoamine oxidase B (MAO-B) which breaks down dopamine secreted by the dopaminergic neurons. The reduction in MAO-B activity results in increased L-DOPA in the striatum. Like dopamine agonists, MAO-B inhibitors used as monotherapy improve motor symptoms and delay the need for levodopa in early disease, but produce more adverse effects and are less effective than levodopa. There are few studies of their effectiveness in the advanced stage, although results suggest that they are useful to reduce fluctuations between on and off periods. An initial study indicated that selegiline in combination with levodopa increased the risk of death, but this was later disproven.

Other drugs such as amantadine and anticholinergics may be useful as treatment of motor symptoms. However, the evidence supporting them lacks quality, so they are not first choice treatments. In addition to motor symptoms, PD is accompanied by a diverse range of symptoms. A number of drugs have been used to treat some of these problems. Examples are the use of quetiapine for psychosis, cholinesterase inhibitors for dementia, and modafinil for daytime sleepiness. A 2010 meta-analysis found that nonsteroidal anti-inflammatory drugs (apart from aspirin), have been associated with at least a 15 percent (higher in long-term and regular users) reduction of incidence of the development of Parkinson's disease Treating motor symptoms with surgery was once a common practice, but since the discovery of levodopa, the number of operations declined. Studies in the past few decades have led to great improvements in surgical techniques, so that surgery is again being used in people with advanced PD for whom drug therapy is no longer sufficient. Surgery for PD can be divided in two main groups: lesional and deep brain stimulation (DBS). Target areas for DBS or lesions include the thalamus, the globus pallidus or the subthalamic nucleus. Deep brain stimulation is the most commonly used surgical treatment, developed in the 1980s by Alim Louis Benabid and others. It involves the implantation of a medical device called a neurostimulator, which sends electrical impulses to specific parts of the brain. DBS is recommended for people who have PD with motor fluctuations and tremor inadequately controlled by medication, or to those who are intolerant to medication, as long as they do not have severe neuropsychiatric problems. Other, less common, surgical therapies involve intentional formation of lesions to suppress overactivity of specific subcortical areas. For example, pallidotomy involves surgical destruction of the globus pallidus to control dyskinesia.

Exercise programs are recommended in people with Parkinson's disease. There is some evidence that speech or mobility problems can improve with rehabilitation, although studies are scarce and of low quality. Regular physical exercise with or without physical therapy can be beneficial to maintain and improve mobility, flexibility, strength, gait speed, and quality of life. When an exercise program is performed under the supervision of a physiotherapist, there are more improvements in motor symptoms, mental and emotional functions, daily living activities, and quality of life compared to a self-supervised exercise program at home. In terms of improving flexibility and range of motion for people experiencing rigidity, generalized relaxation techniques such as gentle rocking have been found to decrease excessive muscle tension. Other effective techniques to promote relaxation include slow rotational movements of the extremities and trunk, rhythmic initiation, diaphragmatic breathing, and meditation techniques. As for gait and addressing the challenges associated with the disease such as hypokinesia (slowness of movement), shuffling and decreased arm swing; physiotherapists have a variety of strategies to improve functional mobility and safety. Areas of interest with respect to gait during rehabilitation programs focus on, but are not limited to improving gait speed, the base of support, stride length, trunk and arm swing movement. Strategies include utilizing assistive equipment (pole walking and treadmill walking), verbal cueing (manual, visual and auditory), exercises (marching and PNF patterns) and altering environments (surfaces, inputs, open vs. closed). Strengthening exercises have shown improvements in strength and motor function for people with primary muscular weakness and weakness related to inactivity with mild to moderate Parkinson's disease. However, reports show a significant interaction between strength and the time the medications was taken. Therefore, it is recommended that people with PD should perform exercises 45 minutes to one hour after medications when they are at their best. Also, due to the forward flexed posture, and respiratory dysfunctions in advanced Parkinson's disease, deep diaphragmatic breathing exercises are beneficial in improving chest wall mobility and vital capacity. Exercise may improve constipation.

One of the most widely practiced treatments for speech disorders associated with Parkinson's disease is the Lee Silverman voice treatment (LSVT). Speech therapy and specifically LSVT may improve speech. Occupational therapy (OT) aims to promote health and quality of life by helping people with the disease to participate in as many of their daily living activities as possible. There have been few studies on the effectiveness of OT and their quality is poor, although there is some indication that it may improve motor skills and quality of life for the duration of the therapy.

Palliative care is specialized medical care for people with serious illnesses, including Parkinson's. The goal is to improve quality of life for both the person suffering from Parkinson's and the family by providing relief from the symptoms, pain, and stress of illnesses. As Parkinson's is not a curable disease, all treatments are focused on slowing decline and improving quality of life, and are therefore palliative in nature. Palliative care should be involved earlier, rather than later in the disease course. Palliative care specialists can help with physical symptoms, emotional factors such as loss of function and jobs, depression, fear, and existential concerns.

Along with offering emotional support to both the patient and family, palliative care serves an important role in addressing goals of care. People with Parkinson's may have many difficult decisions to make as the disease progresses such as wishes for feeding tube, non-invasive ventilator, and tracheostomy; wishes for or against cardiopulmonary resuscitation; and when to use hospice care. Palliative care team members can help answer questions and guide people with Parkinson's on these complex and emotional topics to help them make the best decision based on their own values.

Muscles and nerves that control the digestive process may be affected by PD, resulting in constipation and gastroparesis (food remaining in the stomach for a longer period than normal). A balanced diet, based on periodical nutritional assessments, is recommended and should be designed to avoid weight loss or gain and minimize consequences of gastrointestinal dysfunction. As the disease advances, swallowing difficulties (dysphagia) may appear. In such cases it may be helpful to use thickening agents for liquid intake and an upright posture when eating, both measures reducing the risk of choking. Gastrostomy to deliver food directly into the stomach is possible in severe cases.

Levodopa and proteins use the same transportation system in the intestine and the blood-brain barrier, thereby competing for access. When they are taken together, this results in a reduced effectiveness of the drug. Therefore, when levodopa is introduced, excessive protein consumption is discouraged and well balanced Mediterranean diet is recommended. In advanced stages, additional intake of low-protein products such as bread or pasta is recommended for similar reasons. To minimize interaction with proteins, levodopa should be taken 30 minutes before meals. At the same time, regimens for PD restrict proteins during breakfast and lunch, allowing protein intake in the evening.

Repetitive transcranial magnetic stimulation temporarily improves levodopa-induced dyskinesias. Its usefulness in PD is an open research topic, although recent studies have shown no effect by rTMS. Several nutrients have been proposed as possible treatments; however there is no evidence that vitamins or food additives improve symptoms. There is no evidence to substantiate that acupuncture and practice of Qigong, or Tai chi, have any effect on the course of the disease or symptoms. Further research on the viability of Tai chi for balance or motor skills are necessary. Fava beans and velvet beans are natural sources of levodopa and are eaten by many people with PD. While they have shown some effectiveness in clinical trials, their intake is not free of risks. Life-threatening adverse reactions have been described, such as the neuroleptic malignant syndrome.

PD invariably progresses with time. A severity rating method known as the Unified Parkinson's disease rating scale (UPDRS) is the most commonly used metric for clinical study. A modified version known as the MDS-UPDRS is also sometimes used. An older scaling method known as the Hoehn and Yahr scale (originally published in 1967), and a similar scale known as the Modified Hoehn and Yahr scale, have also been commonly used. The Hoehn and Yahr scale defines five basic stages of progression.

Motor symptoms, if not treated, advance aggressively in the early stages of the disease and more slowly later. Untreated, individuals are expected to lose independent ambulation after an average of eight years and be bedridden after ten years. However, it is uncommon to find untreated people nowadays. Medication has improved the prognosis of motor symptoms, while at the same time it is a new source of disability, because of the undesired effects of levodopa after years of use. In people taking levodopa, the progression time of symptoms to a stage of high dependency from caregivers may be over 15 years. However, it is hard to predict what course the disease will take for a given individual. Age is the best predictor of disease progression. The rate of motor decline is greater in those with less impairment at the time of diagnosis, while cognitive impairment is more frequent in those who are over 70 years of age at symptom onset.

Since current therapies improve motor symptoms, disability at present is mainly related to non-motor features of the disease. Nevertheless, the relationship between disease progression and disability is not linear. Disability is initially related to motor symptoms. As the disease advances, disability is more related to motor symptoms that do not respond adequately to medication, such as swallowing/speech difficulties, and gait/balance problems; and also to motor complications, which appear in up to 50% of individuals after 5 years of levodopa usage. Finally, after ten years most people with the disease have autonomic disturbances, sleep problems, mood alterations and cognitive decline. All of these symptoms, especially cognitive decline, greatly increase disability.

The life expectancy of people with PD is reduced. Mortality ratios are around twice those of unaffected people. Cognitive decline and dementia, old age at onset, a more advanced disease state and presence of swallowing problems are all mortality risk factors. On the other hand, a disease pattern mainly characterized by tremor as opposed to rigidity predicts an improved survival. Death from aspiration pneumonia is twice as common in individuals with PD as in the healthy population. In 2013 PD resulted in about 103,000 deaths globally, up from 44,000 deaths in 1990. The death rate increased from an average of 1.5 to 1.8 per 100,000 during that time.

II. Positioning of Electrodes in Subthalmic Nucleus Deep Brain Stimulation

Identification of the optimal location for electrode placement is achieved via two steps: 1) preoperative imaging, placement of bone fiducial markers, and preoperative target planning and trajectory assignment; and 2) stereotactic mapping of the STN nucleus bilaterally. The second step is separated from the first by approximately one week.

Positioning of the electrodes may be accomplished using the WayPoint™ rapid-prototyped stereotactic system (FHC Inc; Bowdoin, Me.). The first procedure involving outpatient imaging and placement of bone fiducial markers, the operative targets, entry points, and identification of landmarks is performed by a neurosurgeon utilizing the WayPoint™ stereotactic software planning algorithm, which includes access to a unique, normalized physiological atlas database located at Vanderbilt University. This software allows for visualization of previously implanted DBS electrodes by the surgeon and can be overlaid on a patient's MRI along with AC-PC coordinates. Thus, the locations of previous successful implants are available to the surgeon for target planning.

During the second procedure by which the STN nucleus is mapped, a microTargeting™ platform is affixed to the previously placed bone anchors. Arrays of 2-4 tungsten microelectrodes (1 M$\Omega$@ 1 kHz) are placed in guide tubes in a "Ben-gun" configuration and advanced with microTargeting™ electrode drives (FHC Inc., Bowdoin, Me.). Microelectrode recording (MER) is performed using either the Leadpoint™ (Medtronic, Inc., Minneapolis, Minn.) or Guideline™ (FHC Inc., Bowdoin, Me.) recording system. The microelectrodes are advanced toward the STN along the predefined trajectory. Recordings are made at regular intervals, beginning above the target and ending below the target or at the dorsal border of the substantia nigra pars reticularis (SNr). The recordings are interpreted based on accepted criteria by a neurophysiologist in the operating room and are used to define the borders of the STN and SNr. Determination of the optimal stimulation target was determined by consensus opinion of the neurosurgeon, neurologist, and neurophysiologist.

A general procedure for the identification of the STN nucleus as well as the determination of the optimal lead locations is outlined in Starr (2002), which discloses "[t]he essential steps in DBS implantation are magnetic-resonance imaging (MRI)-guided stereotactic localization, confirmation of the motor territory of the target nucleus with microelectrode mapping, and intra-operative test stimulation to determine voltage thresholds for stimulation-induced adverse effects." Details regarding methods for the identification of the STN nucleus as well as target selection is taught in Hutchinson et al. (1998), stating "[t]he STN can be identified by the presence of neurons with characteristic 25- to 45-Hz firing rates and irregular firing patterns, which may have movement- or tremor-related activity."

Location selection is the topic of the review presented in Gross et al. (2006), as well as the rationale for employing physiological mapping in addition to standard imaging techniques in order to most accurately map the STN. The ideal locations for electrode placement are determined intraoperatively through microstimulation. Gross recites, "[m]icrostimulation at the site of site where tremor-related neurons were recorded can induce tremor arrest with a short latency . . . [and t]his effect is limited to specific body segments in accordance with the somatotopic arrangement. The use of a wider pulse duration (>0.5 ms) usually spreads the antitremor effect to other body regions after a longer delay (1-2 s)."

III. Combination Treatments

It also may prove advantageous to use combination therapies in the treatment of PD, where a therapy is added to the STN-DBS therapy. Such therapies may, in combination, provide better results that the individual therapies, and in some cases, may provide more than additive effects. In other cases, they may reduce the amount of one or the other therapies required to achieve clinical benefit.

This process may involve administering both therapies at the same time. Alternatively, the STN-DBS therapy may precede or follow the other treatment by intervals ranging from minutes to weeks. In embodiments where the other therapy and STN-DBS are applied separately to the subject, one would generally ensure that a significant period of time did not expire between each delivery, such that the other therapy and STN-DBS would still be able to exert an advantageously combined effect on the subject. In such instances, it is contemplated that one may administer both modalities within about 12-24 h of each other and, more preferably, within about 6-12 h of each other. In some situations, it may be desirable to extend the time period for treatment significantly, however, where one or several days (2, 3, 4, 5, 6 or 7) to several weeks (1, 2, 3, 4, 5, 6, 7 or 8) lapse between the respective administrations.

Various combinations may be employed; for example, the STN-DBS therapy is "A" and the second PD therapy is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

Administration of the therapies to a patient will follow general protocols for the administration of that particular secondary therapy, taking into account the toxicity/side effects, if any, of the treatments. It is expected that the treatment cycles would be repeated as necessary.

As discussed above, while there is no cure for Parkinson's disease, medications, surgery, and multidisciplinary management can provide relief from the symptoms. These therapies include levodopa (usually combined with a DOPA decarboxylase inhibitor like carbidopa and benserazide or a COMT inhibitor, such as tolcapone or entacapone, that does not cross the blood-brain barrier), dopamine agonists (e.g., apomorphine, bromocriptine, pergolide, pramipexole, ropinirole, piribedil, cabergoline, apomorphine and lisuride), MAO-B inhibitors (e.g., safinamide, selegiline and rasagiline), amantadine, anticholinergics cholinesterase inhibitors, and lesional surgery.

IV. Examples

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Methods

The DBS in early stage PD pilot trial was a two-year prospective, randomized, controlled, single-blind study that randomized subjects 1:1 to receive ODT or DBS+ODT (clinicaltrials.gov NCT00282152, FDA IDE # G050016; Vanderbilt IRB #040797) (Charles et al. 2014). At baseline, subjects were age 60.5±6.5, Hoehn & Yahr stage 2.01±0.1 off medication, had a medication duration of 2.2±1.2 years, and were without a history of dyskinesia or other motor fluctuations. The Unified Parkinson's Disease Rating Scale Part III (UPDRS-III) motor examination was videotaped in the OFF therapy state after a seven-day washout of medication and stimulation (if applicable) at baseline and every six months for two years. At the conclusion of the trial, all videotapes were scored in random order by an independent rater blinded to treatment assignment, ON versus OFF therapy status, and study visit chronology. The UPDRS-III score reported here includes all motor items except rigidity which cannot be evaluated by videotape.

Each subject was categorized based on their post-washout change (Δ) in UPDRS-III OFF motor score from baseline to two years as improved (Δ<0), no change (Δ=0), or worsened (Δ>0) (4). Fisher's exact test was used to assess the difference between the ODT and DBS+ODT groups in the risk of motor score worsening (worsened vs. improved or no change). The difference between the two groups in the trend toward worsening was assessed using exact logistic regression of the ordered outcome scores (improved, no change, worsened); the logistic model included the treatment group as the outcome (1=ODT, 0=DBS+ODT) and the change in motor score from baseline to two years as an ordered score (improved=0, no change=1, worsened=2) as the only explanatory variable. The difference in trend towards worsening was assessed using the estimated odds ratio for the ordered score. Analyses were conducted in SAS 9.3 (SAS Institute Inc., Cary, N.C.).

Example 2—Results

UPDRS-III OFF motor score from baseline to two years worsened for all subjects randomized to receive ODT (14/14; Table 1). By contrast, UPDRS-III OFF motor score did not worsen for 5 out of 14 randomized to receive DBS+ODT (p=0.04, Fisher's exact test for no difference between treatment groups in risk of motor score worsening). Moreover, the UPDRS-III OFF therapy score at two years was improved compared to their baseline scores for four of the five DBS+ODT subjects whose motor scores did not worsen at two years. Compared to the DBS+ODT group, the ODT group had a nearly four-fold increased chance of worsening (exact logistic regression median unbiased estimated odds ratio, ODT vs. ODT+DBS=3.68, P=0.04).

TABLE 1

Motor symptom worsening from baseline to two years.

| Treatment Group | Improved (change in score < 0): | No change (change in score = 0): | Worsened (change in score ≥ 0): | Total no. of subjects |
|---|---|---|---|---|
| ODT | 0 | 0 | 14 | 14 |
| DBS + ODT | 4 | 1 | 9 | 14 |
| Total no. of subjects | 4 | 1 | 23 | 28 |

The ODT group had a nearly 4-fold increased chance of worsening compared to the DBS + ODT group [median unbiased estimated (MUE) odds ratio for ordered outcome score, ODT vs. DBS + ODT = 3.68, P = 0.04.]

Figure 1A:
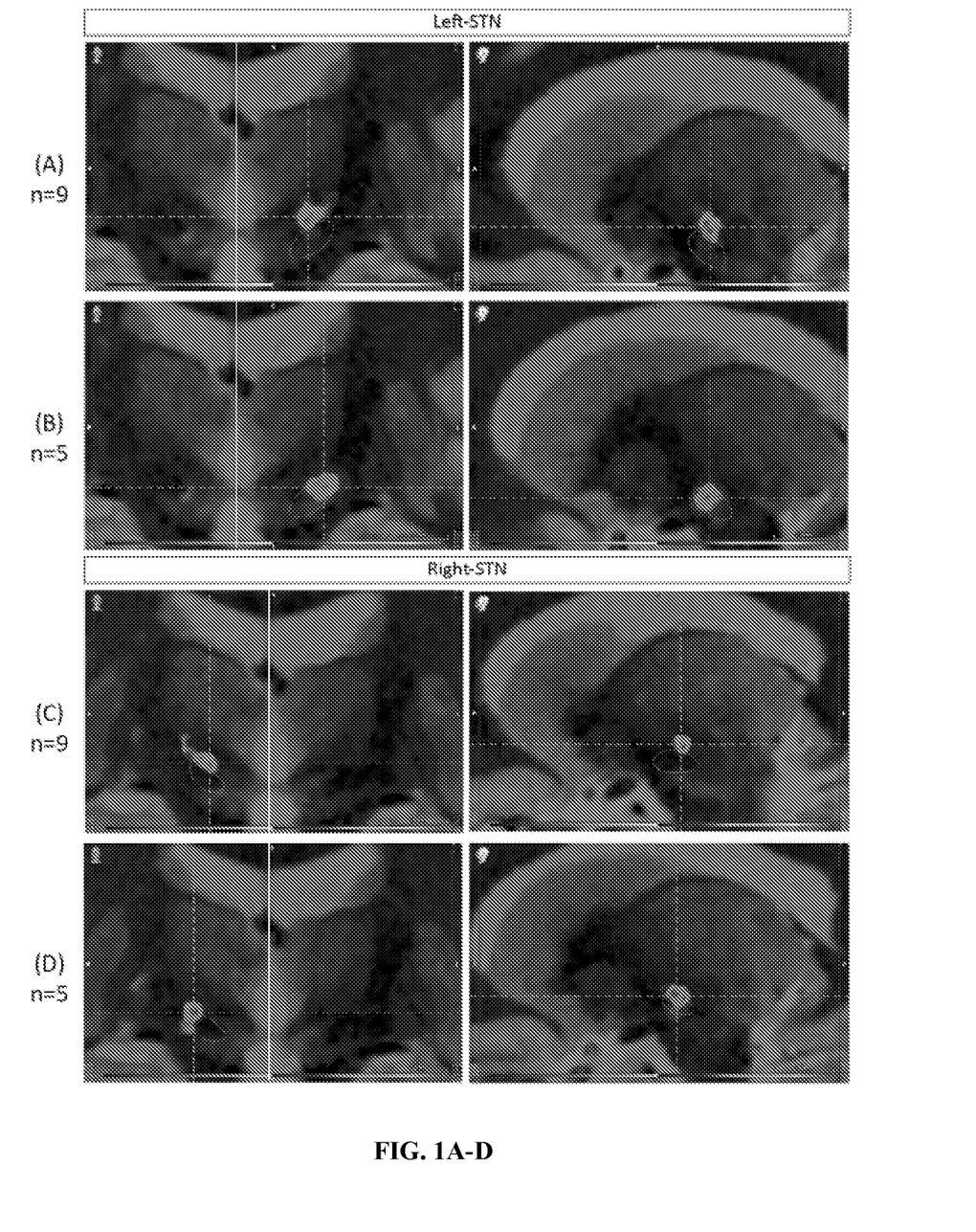
Figure 2:
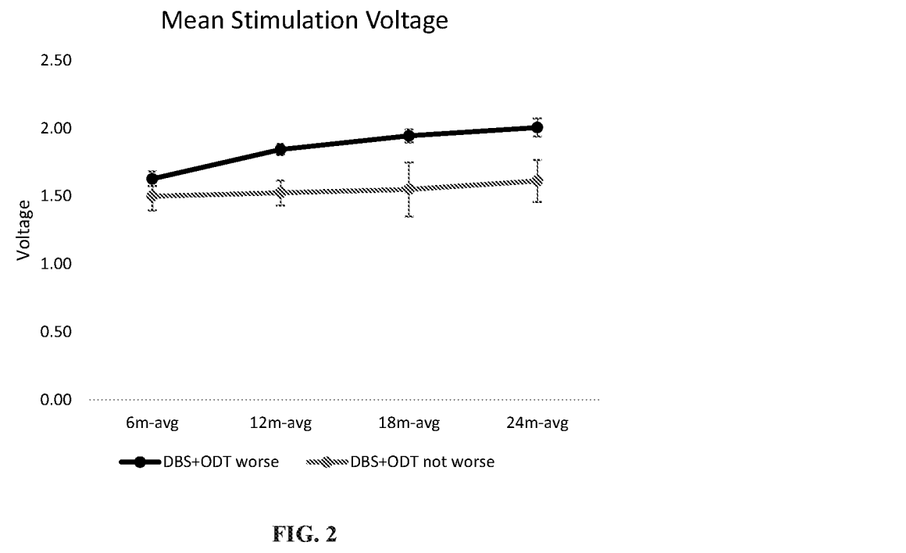
FIG. 2: Stimulation Levels (tabular data shown in Table 2).
Figure 3:
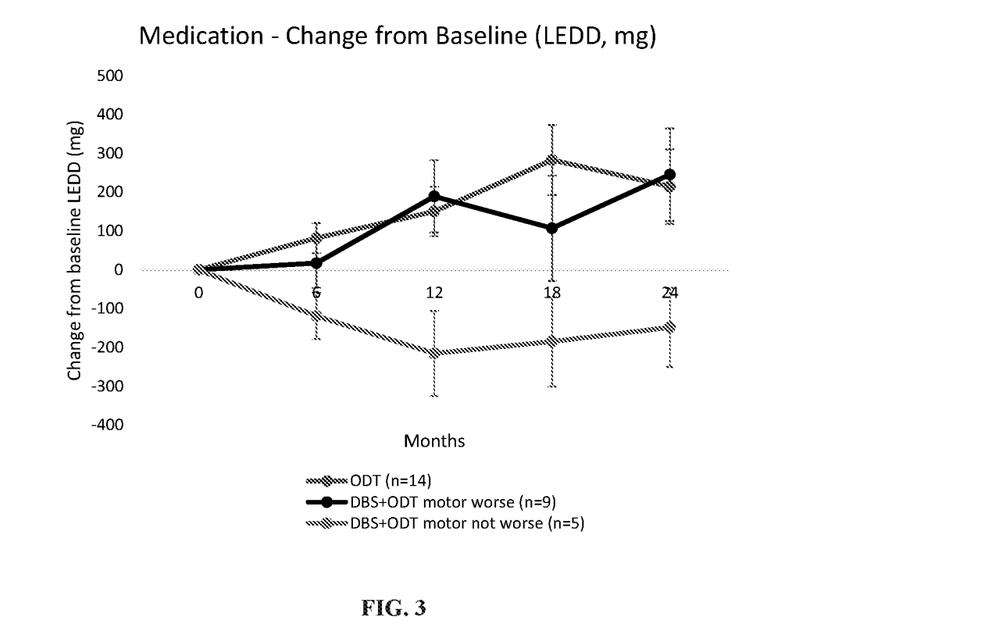
FIG. 3: Change in Medication Levels (tabular data shown in Table 2).

The two bilateral STN-DBS groups ("motor worsened" versus "motor not-worsened") were compared based on post-operative MRI data and programming data from the 24-month follow-up visit (location of the active contact and level of stimulation). There were 18 leads in 9 subjects in the "motor worsened" group (left+right) and 10 leads in 5 subjects in the "motor not-worsened" group (left+right). Mean STN stimulation (voltage) and PD medication levels (LEDD, mg) were evaluated throughout the two-year study period. The lateral inferior position of the stimulating contact within the STN (FIGS. 1A-D) led to slowing motor symptom progression (Table 1), lower stimulation parameters (FIG. 2, Table 2), and less need for postoperative dopaminergic medication.

TABLE 2

STIMULATION LEVELS (VOLTS)

| Group | 6 months | 12 months | 18 months | 24 months |
|---|---|---|---|---|
| Motor Worsened (n = 9) | 1.63 ± 0.16 | 1.84 ± 0.12 | 1.94 ± 0.14 | 2.01 ± 0.20 |
| Motor Not-Worsened (n = 5) | 1.50 ± 0.23 | 1.53 ± 0.21 | 1.55 ± 0.44 | 1.61 ± 0.35 |

TABLE 3

MEDICATION CHANGE FROM BASELINE (LEDD, MG)

| Group | 6 months | 12 months | 18 months | 24 months |
|---|---|---|---|---|
| ODT Motor Worsened (n = 14) | 81.7 ± 39.0 | 150.4 ± 63.7 | 283.0 ± 90.6 | 214.5 ± 96.2 |
| DBS Motor Worsened (n = 9) | 17.1 ± 63.3 | 189.2 ± 93.3 | 107.1 ± 135.3 | 245.3 ± 118.9 |
| DBS Motor Not-Worsened (n = 5) | −119.2 ± 59.1 | −215.6 ± 109.2 | −185.0 ± 115.4 | −148.4 ± 101.7 |

Example 3—Conclusion

More than one-third of early stage PD subjects treated with DBS+ODT in this pilot trial did not experience motor symptom worsening after two years, while motor symptoms worsened for all subjects treated with ODT alone. Given the expectation of universal motor function worsening as PD progresses, these results suggest that DBS may slow motor symptom progression for a significant portion of early stage PD patients. Future studies are designed to confirm this finding, and the FDA has approved the conduct of a prospective, randomized, double-blind, placebo-controlled, multicenter, phase III, pivotal clinical trial testing STN DBS in very early stage PD in 280 subjects at twenty U.S. centers (IDE # G050016).

All of the compositions and/or methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

V. References

The following references, to the extent that they provide exemplary procedural or other details supplementary to those set forth herein, are specifically incorporated herein by reference.

Stan, P. A., *Stereotact. Funct. Neurosurg.* 2002, 79: 118-145.
Hutchinson et al., *Ann. Neurol.* 1998 44(4): 622-8.
Gross et al., *Mov. Disord.* 2006, 21(14): S259-S283.
Charles et al., *Parkinsonism & Related Disorders.* 2014; 20(7):731.
Wallace et al., *Brain.* 2007; 130(8):2129.
Spieles-Engemann et al., *Neurobiology of Disease.* 2010; 39(1):105.
Nestor et al., *PLoS ONE.* 2014; 9(4):e93524.
Kahn et al., Journal of Neurology, *Neurosurgery, and Psychiatry* 2012; 83(2):164-170.
Plaha et al., *Brain* 2006; 129(7):1732-1747.
McClelland et al., J Clin Neurosci. 2009; 16: 771-778.
Caire et al., *Stereotact Funct Neurosurg.* 2009; 87: 337-347.
Schlaier et al., *Neurosurg Rev.* 2014; 37: 461-470.
Herzog et al., *Mov Disord.* 2004; 19(9):1050-1054.
Voges et al., *J Neurosurg.* 2002; 96(2): 269-279.
Yelnik et al., *J Neurosurg.* 2003; 99(1):89-99.
Wodarg et al., *Mov Disord.* 2012; 27(7):874-9.

What is claimed:

1. A method of treating Parkinson's Disease (PD) in an early stage PD subject comprising administering to said subject subthalamic nucleus (STN) deep brain stimulation (DBS) over a period of at least two years by positioning a DBS electrode in the margin of the dorsal-lateral and anterior region of the subthalamic nucleus and applying electrical current to said subject through said electrode, wherein treating comprises one or more of slowing of motor symptom progression, stopping motor symptom progression, and/or reversing motor symptom progression as measured at two years from the start of STN-DBS.

2. The method of claim 1, wherein said subject is a human subject.

3. The method of claim 2, wherein said subject is a male human subject.

4. The method of claim 2, wherein said subject is a female human subject.

5. The method of claim 1, wherein said subject is a non-human mammalian subject.

6. The method of claim 1, wherein DBS is performed more than once.

7. The method of claim 6, wherein DBS in performed on a chronic basis.

8. The method of claim 1, further comprising treating said subject with a second PD therapy.

9. The method of claim 8, wherein said second PD therapy is administered prior to STN-DBS.

10. The method of claim 8, wherein said second PD therapy is administered at the same time as STN-DBS.

11. The method of claim 8, wherein said second PD therapy is administered after STN-DBS.

12. The method of claim 8, wherein said second PD therapy is selected from levodopa, optionally in combination with a DOPA decarboxylase inhibitor (carbidopa, benserazide) or a COMT inhibitor (tolcapone, entacapone), a dopamine agonist (e.g., apomorphine, bromocriptine, pergolide, pramipexole, ropinirole, piribedil, cabergoline, apomorphine, lisuride), an MAO-B inhibitor (e.g., safinamide, selegiline, rasagiline), amantadine, an anticholinergics cholinesterase inhibitor, and lesional surgery, or combinations thereof.

13. The method of claim 1, wherein STN-DBS further results in one or more of lower stimulation parameters, less need for post-operative dopaminergic medication, and/or less development of levodopa associated dyskinesia or other motor fluctuations.

14. The method of claim 1, wherein the margin of the dorsal-lateral and anterior region of the subthalamic nucleus is defined by imaging and/or micro-electrode recording that defines the subthalamic nucleus.

15. The method of claim 1, wherein imaging comprises (a) preoperative imaging and preoperative stereotactic target planning and trajectory assignment; and (b) stereotactic mapping of the STN nucleus bilaterally.

16. The method of claim 1, wherein the margin of the dorsal-lateral and anterior region of the subthalamic nucleus is defined electrophysiologically by the anterior border of the STN through its relationship with the internal capsule and the dorsal margin of STN.

17. The method of claim 16, wherein electrophysiologic identification comprises the insertion of microelectrodes into the region of STN, having an exposed recording surface small enough to detect unit firing activity as measured by impedance greater than 150K ohms, and continuous measurement of spontaneous neural firing activity while passing the microelectrodes through the region dorsal to STN and into the STN.

18. The method of claim 17, wherein the firing rate changes significantly upon transitioning from white matter tracts just above or anterior to the STN to the neuronal activity seen within the STN by a factor of 5 or more.

* * * * *

UNITED STATES PATENT AND TRADEMARK OFFICE
CERTIFICATE OF CORRECTION

| | | |
|---|---|---|
| PATENT NO. | : 11,577,079 B2 | Page 1 of 1 |
| APPLICATION NO. | : 16/500986 | |
| DATED | : February 14, 2023 | |
| INVENTOR(S) | : David Charles et al. | |

It is certified that error appears in the above-identified patent and that said Letters Patent is hereby corrected as shown below:

In the Specification

In Column 1, Lines 13-18, please delete the paragraph and insert:
--This invention was made with government support under Grant Nos. EB006136, TR000011, and TR000445, awarded by the National Institutes of Health. The government has certain rights in the invention.-- therefor.

Signed and Sealed this
Twenty-sixth Day of September, 2023

Katherine Kelly Vidal
*Director of the United States Patent and Trademark Office*